United States Patent [19]
Mattox

[11] Patent Number: 5,955,486
[45] Date of Patent: Sep. 21, 1999

[54] STABLE MICROBICIDE FORMULATION

[75] Inventor: John Robert Mattox, Perkasie, Pa.

[73] Assignee: Rohm and Haas Company, Philadelphia, Pa.

[21] Appl. No.: 09/023,447

[22] Filed: Feb. 13, 1998

Related U.S. Application Data

[60] Provisional application No. 60/063,351, Oct. 28, 1997.

[51] Int. Cl.⁶ .......................... A01N 43/80; A01N 25/22; A01N 59/20; A01N 59/00
[52] U.S. Cl. .......................... 514/372; 514/373; 514/970; 514/971; 514/973; 424/661; 424/662; 424/630; 424/632; 424/633; 424/634; 424/635; 424/637; 424/638; 504/151; 504/156
[58] Field of Search .................................... 514/372–373, 514/970, 971, 973; 424/661, 662, 630, 632–635, 637–638; 504/151, 156

[56] References Cited

U.S. PATENT DOCUMENTS

| | | | |
|---|---|---|---|
| 3,870,795 | 3/1975 | Miller et al. | 514/372 |
| 4,396,413 | 8/1983 | Miller et al. | 504/152 |
| 5,118,699 | 6/1992 | Willingham et al. | 514/372 |
| 5,127,934 | 7/1992 | Mattox | 514/372 |
| 5,145,501 | 9/1992 | Lashen et al. | 514/372 |
| 5,153,213 | 10/1992 | Schmidt | 514/372 |
| 5,160,527 | 11/1992 | Law et al. | 504/156 |
| 5,461,150 | 10/1995 | Gironda et al. | 548/213 |
| 5,599,827 | 2/1997 | Gironda | 514/372 |
| 5,670,529 | 9/1997 | Clarke | 514/360 |

FOREIGN PATENT DOCUMENTS

| | | |
|---|---|---|
| 0 606 986 A1 | 7/1994 | European Pat. Off. . |
| 0721736 A1 | 7/1996 | European Pat. Off. . |
| 0749689 A2 | 12/1996 | European Pat. Off. . |

*Primary Examiner*—John Pak
*Attorney, Agent, or Firm*—S. Matthew Cairns

[57] ABSTRACT

Stable microbicidal compositions containing a 3-isothiazolone compound, chlorate or perchlorate salts, copper salts and water are disclosed. Also disclosed are methods of preventing or reducing precipitate formation in 3-isothiazolone compositions.

10 Claims, No Drawings

STABLE MICROBICIDE FORMULATION

This application claims the benefit of priority of U.S. Provisional Application No. 60/063,351, which was filed on Oct. 28, 1997.

BACKGROUND OF THE INVENTION

This invention relates to the stabilization of microbicides. In particular, this invention relates to the improved stabilization of 3-isothiazolone concentrate compositions.

Microbicides are used commercially to prevent the growth of microbes in a variety of loci, such as cooling towers, metal working fluid systems, paint and cosmetics. One of the more important classes of microbicides is 3-isothiazolones. Many 3-isothiazolones have achieved commercial success because they are very effective in preventing microbial growth under a wide variety of conditions and in a variety of loci. Among the most important 3-isothiazolones are 5-chloro-2-methyl-3-isothiazolone, 2-methyl-3-isothiazolone, and mixtures thereof.

While 3-isothiazolones are very effective microbicides, they suffer from being unstable under certain conditions. Without the presence of a stabilizer, many 3-isothiazolones chemically degrade and lose microbicidal efficacy. Much research has been devoted to stabilizing 3-isothiazolones.

In general, compounds that stabilize 3-isothiazolone concentrates do not stabilize 3-isothiazolone dilute solutions. Compounds, such as magnesium nitrate, that do stabilize both 3-isothiazolone concentrates and dilute solutions do so in greatly differing amounts. More magnesium nitrate is required to stabilize a 3-isothiazolone dilute solution than a concentrate; 23 percent by weight for dilute solutions as compared to 12 to 16 percent by weight for concentrates. As dilute solutions are typically prepared by diluting 3-isothiazolone concentrate compositions, this need for additional stabilizer results in increased cost and handling.

Typical 3-isothiazolone products of a 3:1 mixture of 5-chloro-2-methyl-3-isothiazolone and 2-methyl-3-isothiazolone contain between 1 and 25 percent by weight of the 3-isothiazolone mixture and a similar amount of a stabilizer. Concentrate compositions of a 3:1 mixture of 5-chloro-2-methyl-3-isothiazolone and 2-methyl-3-isothiazolone generally contain about 5 to 35 percent by weight of the 3-isothiazolone compounds and require about 10 to 25 percent by weight of a stabilizer, such as magnesium nitrate. Dilute solutions of a 3:1 mixture of 5-chloro-2-methyl-3-isothiazolone and 2-methyl-3-isothiazolone contain about 0.5 to 5 percent by weight of the 3-isothiazolone compounds.

A variety of stabilizers for 3-isothiazolone concentrates are known. These known stabilized 3-isothiazolone dilute solutions suffer from having a high metal salt content or from having limited stability. When a 3-isothiazolone stabilized with a metal salt is added to a latex formulation, the high metal salt content can coagulate the latex. U.S. Pat. No. 5,145,501 (Lashen, et al.), herein incorporated by reference, discloses the stabilization of 3-isothiazolone concentrates with a metal bromate salt. The problem with these compositions is that any non-halogenated isothiazolones become brominated upon storage, resulting in limited stability of the 3-isothiazolones. This patent also teaches that chlorate and perchlorate salts do not stabilize 3-isothiazolones. Moreover, this patent does not address the problem of precipitate formation upon storage of the 3-isothiazolone compositions.

Although the use of stabilizers enables 3-isothiazolone products to retain their microbicidal efficacy for considerable periods of time, other problems may develop without significant loss of 3-isothiazolones, such as the formation of precipitate upon storage. The presence of this precipitate does not impact the efficacy of the 3-isothiazolones; however, the presence of the precipitate gives an undesirable appearance to users of the product. It is clearly preferable from a commercial standpoint to have a product which does not form a precipitate.

Thus, there is a continuing need for stable 3-isothiazolone concentrate compositions that remain stable when diluted to form dilute solutions without the need for additional stabilizer and are free of precipitate.

SUMMARY OF THE INVENTION

It has now been found that 3-isothiazolone concentrate compositions can be effectively stabilized by chlorate or perchlorate salts in the presence of a small amount of cupric ion in the form of a copper salt while avoiding the problems of salt shock, limited stability of the 3-isothiazolones, and precipitate formation upon storage.

The present invention is directed to a stable microbicide composition including: (a) 5 to 35 wt %, based on the weight of the composition, of a water soluble 3-isothiazolone; (b) 0.2 to 20 wt %, based on the weight of the composition, of a chlorate or perchlorate salt; (c) 0.01 to 3 wt %, based on the weight of the composition, of a cupric ion in the form of a copper salt; and (d) water; wherein the weight ratio of (b) to (c) is 6:1 to 200:1; and the composition is precipitate free.

The present invention is also directed to a method of stabilizing a microbicide composition including the step of adding 0.2 to 20 wt %, based on the weight of the composition, of a chlorate or perchlorate salt; and 0.01 to 10 wt %, based on the weight of the composition, of a cupric ion in the form of a copper salt to a 3-isothiazolone composition comprising 5 to 35 wt %, based on the weight of the composition, of a water soluble 3-isothiazolone compound; and water; wherein the weight ratio of the chlorate or perchlorate salt to the copper salt is 15:1 to 200:1.

The present invention is also directed to a method of controlling or inhibiting the growth of microorganisms in a locus including introducing to the locus a composition as described above.

DETAILED DESCRIPTION OF THE INVENTION

As used throughout the specification, the following terms shall have the following meanings, unless the context clearly indicates otherwise.

The term "microbicide" refers to a compound capable of inhibiting the growth of or controlling the growth of microorganisms at a locus. The term "microorganism" includes, but is not limited to, fungi, bacteria, and algae. The term "locus" refers to an industrial system or product subject to contamination by microorganisms.

As used in this specification, the following abbreviations are applied: HPLC=high performance liquid chromatography; C=centigrade; ppm=parts per million; g=gram; DI=deionized; mL=milliliter; and wt %=percent by weight.

All amounts are percent by weight, unless otherwise noted and all percent by weight ranges are inclusive. All ratios are by weight and all ratio ranges are inclusive.

Any water soluble 3-isothiazolone compound is useful in the compositions of the present invention. Water soluble 3-isothiazolone compounds are those having a water solubility greater than 1000 ppm. Suitable 3-isothiazolone compounds include, but are not limited to: 5-chloro-2-methyl-3-isothiazolone; 2-methyl-3-isothiazolone; 2-ethyl-3-isothiazolone; 5-chloro-2-ethyl-3-isothiazolone; 4,5-dichloro-2-methyl-3-isothiazolone; and mixtures thereof. Preferred 3-isothiazolones are 5-chloro-2-methyl-3- isothiazolone and 2-methyl-3-isothiazolone, either alone or in admixture. When mixtures of 5-chloro-2-methyl-3-isothiazolone and 2-methyl-3-isothiazolone are used, the weight ratio of 5-chloro-2-methyl-3-isothiazolone to 2-methyl-3-isothiazolone is generally 99:1 to 1:99, preferably 10:1 to 3:1.

The amount of water soluble 3-isothiazolone compound useful in the compositions of the present invention is 5 to 35 wt %, based on the weight of the composition. It is preferred that the amount of 3-isothiazolone compound is 5 to 25 wt %; and more preferably, 10 to 25 wt %.

Any water soluble chlorate or perchlorate salt may be used in the compositions of the present invention. Suitable chlorate or perchlorate salts include, but are not limited to: sodium chlorate, potassium chlorate, sodium perchlorate, and potassium perchlorate. Sodium chlorate and potassium chlorate are preferred. More than one chlorate or perchlorate salt may be used advantageously in the compositions of the present invention.

The amount of chlorate or perchlorate salt useful in the compositions of the present invention is 0.2 to 20 wt %, based on the weight of the composition. It is preferred that the amount of chlorate or perchlorate salt is 1 to 10 wt %, and more preferably 2 to 8 wt %. The chlorate or perchlorate salts are generally commercially available, for example, from Aldrich Chemical Company (Milwaukee, Wisconsin), and may be used without further purification.

A wide variety of copper salts are known in the art. Any copper salt which is sufficiently water soluble to provide the desired level of cupric ion in solution may be used in the compositions of the present invention. Suitable examples include, but are not limited to: copper sulfate, copper acetate, copper chloride, copper bromide, copper chlorate, copper perchlorate, copper nitrite and copper nitrate. Copper sulfate and copper nitrate are preferred. The copper salts are generally commercially available, for example, from Pfalz and Bauer (Waterbury, Connecticut), and may be used without further purification. Mixtures of copper salts may also be used.

The amount of copper salt useful in the compositions of the present invention is 0.01 to 3 wt %, based on the weight of the composition, preferably 0.05 to 2 wt %, and more preferably 0.1 to 1.5 wt %.

The weight ratio of chlorate or perchlorate salt to copper salt is typically 6:1 to 200:1, preferably 20:1 to 100:1, and most preferably 25:1 to 50:1.

Particularly useful compositions of the present invention include 5 to 25 wt % of a water soluble 3-isothiazolone selected from the group consisting of 5-chloro-2-methyl-3-isothiazolone; 2-methyl-3-isothiazolone; and mixtures thereof; 1 to 10 wt % of a sodium chlorate or potassium chlorate; 0.05 to 8 wt % cupric ion in the form of a copper salt; and water. All percentages used above are based on the weight of the composition.

In preparing the compositions of the present invention, the chlorate or perchlorate salt cannot be added directly to the 3-isothiazolone alone. Otherwise, the 3-isothiazolone, chlorate or perchlorate salt, copper salt, and water can be mixed in any order. The compositions of the present invention are preferably prepared by adding the chlorate or perchlorate salt to a mixture of 3-isothiazolone, copper salt, and water.

An advantage of the compositions of the present invention is that they show no visible precipitate formation, even after storage for 12 weeks at 55° C. Even dilute solutions prepared by diluting 3-isothiazolone concentrates of the present invention comprising 3-isothiazolone compounds, chlorate or perchlorate salts, cupric ion in the form of a copper salt, and water, are not only stable against chemical degradation, but are also precipitate free upon storage. Dilute solutions prepared according to the present invention do not need additional stabilizer, thus reducing the cost and extra handling associated with known 3-isothiazolone concentrates. One of the further advantages of the present invention is that the 3-isothiazolone concentrates do not cause coagulation when added to latexes.

The compositions of the present invention can be used to inhibit the growth of microorganisms by introducing a microbicidally effective amount of the compositions onto, into, or at a locus subject to microbial attack. Suitable loci include, but are not limited to: cooling towers; air washers; boilers; mineral slurries; wastewater treatment; ornamental fountains; reverse osmosis filtration; ultrafiltration; ballast water; evaporative condensers; heat exchangers; pulp and paper processing fluids; plastics; emulsions and dispersions; paints; latexes; coatings, such as varnishes; construction products, such as mastics, caulks, and sealants; construction adhesives, such as ceramic adhesives, carpet backing adhesives, and laminating adhesives; industrial or consumer adhesives; photographic chemicals; printing fluids; household products, such as bathroom disinfectants or sanitizers; cosmetics and toiletries; shampoos; soaps; detergents; industrial disinfectants or sanitizers, such as cold sterilants, hard surface disinfectants; floor polishes; laundry rinse water; metalworking fluids; conveyor lubricants; hydraulic fluids; leather and leather products; textiles; textile products; wood and wood products, such as plywood, chipboard, flakeboard, laminated beams, oriented strandboard, hardboard, and particleboard; petroleum processing fluids; fuel; oilfield fluids, such as injection water, fracture fluids, and drilling muds; agriculture adjuvant preservation; surfactant preservation; medical devices; diagnostic reagent preservation; food preservation, such as plastic or paper food wrap; pools; and spas. Preferred loci are cooling towers; air washers; boilers; mineral slurries; wastewater treatment; ornamental fountains; reverse osmosis filtration; ultrafiltration; ballast water; evaporative condensers; heat exchangers; pulp and paper processing fluids; plastics; emulsions and dispersions; paints; latexes; coatings; and metal working fluids.

The amount of 3-isothiazolone compounds suitable to inhibit or control the growth of microorganisms is well known in the art and depends upon the locus to be protected. The amount of 3-isothiazolone microbicide suitable to inhibit the growth of microorganisms is generally between 0.05 and 5,000 ppm, based on the locus to be protected. It is preferred to use between 0.1 and 2,500 ppm. For example, loci such as a cooling tower or pulp and paper processing fluids require 0.1 to 100 ppm of the 3-isothiazolone microbicides to inhibit microorganism growth. In cooling towers or pulp and paper processing fluids, it is preferred to use between 0.1 and 50 ppm. Other loci, such as construction products, oilfield fluids or emulsions, require 0.5 to 5000 ppm of the 3-isothiazolone microbicides to inhibit microorganism growth, while loci such as disinfectants or sanitizers may require up to 5,000 ppm.

It is known in the art that the performance of antimicrobial agents may be enhanced by combination with one or more other antimicrobial agents. Thus, other known microbicidal agents may be combined advantageously with the compositions of the present invention.

The following examples are presented to illustrate further various aspects of the present invention, but are not intended to limit the scope of the invention in any aspect. In the following examples, samples were considered stable when at least 85 percent of the 3-isothiazolones remained after 2 weeks of storage at 55° C.

EXAMPLE 1

Two 3-isothiazolone concentrate samples were prepared according to Table 1. The 3-isothiazolones used were an approximate 3:1 mixture of 5-chloro- 2-methyl-3-isothiazolone ("CMI") and 2-methyl-3-isothiazolone ("MI"). The samples were prepared by combining the 3-isothiazolone and water followed by the addition of any stabilizer. The amounts of each component in Table 1 are reported in wt %. The samples were stored in an oven at 55° C. and analyzed by HPLC for the percentage of CMI remaining after 1 and 2 weeks storage. The results are reported in Table 2.

TABLE 1

| Sample | CMI + MI | Water | Copper Sulfate (wt %) | Sodium Chlorate (wt %) |
|---|---|---|---|---|
| Comparative | 15 | 81.0 | — | 4.0 |
| A | 15 | 80.9 | 0.1 | 4.0 |

TABLE 2

| Sample | 1 Week | 2 Weeks |
|---|---|---|
| Comparative | 0 | 0 |
| A | 98 | 96 |

The above data clearly show that the combination of cupric ion and chlorate provides greater stability of 3-isothiazolone concentrates than cupric ion alone.

EXAMPLE 2

The samples prepared according to Example 1 were also visually inspected for the presence of precipitate when the samples were prepared and at various times during storage at 55° C. The results are reported in Table 3.

TABLE 3

| Sample | 0 Days | 5 Days | 90 Days |
|---|---|---|---|
| Comparative | —* | + | + |
| A | — | — | — |

*no precipitate present;
"+"= precipitate present

The above data clearly show that the combination of low levels of cupric ion and chlorate provides 3-isothiazolone concentrate compositions that are precipitate free.

EXAMPLE 3 (COMPARATIVE)

This example demonstrates the effect of cupric ion alone as a stabilizer for 3-isothiazolone concentrates. The sample was prepared by adding 0.59 g copper sulfate (64% anhydrous), 8.17 g DI water and 1.24 g 3-isothiazolones (as a 3:1 mixture 5-chloro-2-methyl-3-isothiazolone and 2-methyl-3-isothiazolone) to a 30 mL glass, screw cap vial. The vial was capped, shaken and stored in an oven at 40° C. This sample contained 12 wt % 3-isothiazolones and 1.5 wt % (15000 ppm) cupric ion. The sample was analyzed by HPLC for the percentage of 5-chloro-2-methyl-3-isothiazolone ("CMI") remaining after 1 and 2 weeks storage. The results are reported in Table 4.

TABLE 4

| Sample | Cupric Ion (wt %) | 1 Week | 2 Weeks |
|---|---|---|---|
| Comparative | 1.5 | 16 | 1 |

The above data clearly show that cupric ion alone does not stabilize 3-isothiazolone concentrates.

What is claimed is:

1. A stable microbicide composition comprising:

(a) 5 to 35 wt %, based on the weight of the composition, of a water soluble 3-isothiazolone;

(b) 0.2 to 20 wt %, based on the weight of the composition, of a chlorate or perchlorate salt;

(c) 0.01 to 3 wt %, based on the weight of the composition, of a cupric ion in the form of a copper salt; and (d) water;

wherein the weight ratio of (b) to (c) is 6:1 to 200:1; and the composition is precipitate free.

2. The composition of claim 1 where the 3-isothiazolone is selected from the group consisting of: 5-chloro-2-methyl-3-isothiazolone; 2-methyl-3-isothiazolone; 2-ethyl-3-isothiazolone; 5-chloro-2-ethyl-3-isothiazolone; 4,5-dichloro-2-methyl-3-isothiazolone; and mixtures thereof.

3. The composition of claim 1 wherein the chlorate or perchlorate salt is selected from the group consisting of: sodium chlorate, potassium chlorate, sodium perchlorate, and potassium perchlorate.

4. The composition of claim 1 wherein the copper salt is selected from the group consisting of: copper sulfate, copper acetate, copper chloride, copper bromide, copper chlorate, copper perchlorate, copper nitrite and copper nitrate.

5. The composition of claim 1 wherein the 3-isothiazolone is selected from the group consisting of: 5-chloro-2-methyl-3-isothiazolone; 2-methyl-3-isothiazolone; and mixtures thereof; and the chlorate or perchlorate salt is selected from the group consisting of: sodium chlorate, potassium chlorate, sodium perchlorate, and potassium perchlorate.

6. A method of stabilizing a microbicide composition comprising the step of adding 0.2 to 20 wt %, based on the weight of the composition, of a chlorate or perchlorate salt; and 0.01 to 3 wt %, based on the weight of the composition, of a cupric ion in the form of a copper salt to a 3-isothiazolone composition comprising 5 to 35 wt %, based on the weight of the composition, of a water soluble 3-isothiazolone compound; and water; wherein the weight ratio of the chlorate or perchlorate salt to the copper salt is 6:1 to 200:1.

7. The method of claim 6 wherein the copper salt is selected from the group consisting of: copper sulfate, copper acetate, copper chloride, copper bromide, copper chlorate, copper perchlorate, copper nitrite and copper nitrate.

8. The method of claim 6 wherein the oxidant is selected from the group consisting of: sodium chlorate, potassium chlorate, sodium perchlorate, and potassium perchlorate.

9. A method of controlling or inhibiting the growth of microorganisms in a locus comprising introducing to the locus the composition of claim 1.

10. The method of claim 9 wherein the locus is selected from the group consisting of: cooling towers; air washers; boilers; mineral slurries; wastewater treatment; ornamental fountains; reverse osmosis filtration; ultrafiltration; ballast water; evaporative condensers; heat exchangers; pulp and paper processing fluids; plastics; emulsions and dispersions; paints; latexes; coatings; and metal working fluids.

* * * * *